United States Patent [19]

Williams

[11] 4,085,326

[45] Apr. 18, 1978

[54] RADIATION REFLECTION METHOD AND APPARATUS PARTICULARLY FOR GAUGING MATERIALS EXHIBITING BROADBAND ABSORPTION OR SCATTERING, OR SIMILAR EFFECTS

[75] Inventor: Paul Williams, Columbus, Ohio

[73] Assignee: Industrial Nucleonics Corporation, Columbus, Ohio

[21] Appl. No.: 734,007

[22] Filed: Oct. 19, 1976

[51] Int. Cl.$^2$ .................... G01T 1/16; G01J 3/00
[52] U.S. Cl. ................................ 250/339; 250/340; 250/341
[58] Field of Search ............... 250/339, 341, 340

[56] References Cited

U.S. PATENT DOCUMENTS

| | | | |
|---|---|---|---|
| 3,631,526 | 12/1971 | Brunton | 250/341 |
| 3,803,414 | 4/1974 | Van Horne et al. | 250/339 |
| 3,863,071 | 1/1975 | Campanella | 250/339 |
| 3,870,884 | 3/1975 | Williams | 250/339 |

Primary Examiner—Archie R. Borchelt
Attorney, Agent, or Firm—C. Henry Peterson

[57] ABSTRACT

Methods and apparatus are provided for gauging the thickness or other property of a plastic film such as blown film or other material having a front side, a back side, and characteristics including a substantial transparency to radiation at a reference wavelength and a degree of transparency depending on the value of the property at an absorption wavelength. These methods and apparatus provide a useful measurement of the material property in the presence or absence of detrimental effects such as those caused by a broadband absorbing substance (e.g. carbon black) or scattering substance (e.g. $TiO_2$) in the material, or variations in the apparent reflectivity of one or both of the surfaces on the front and back sides, as a result, for example, of the minute surface irregularities in high-density polyethylene. Radiations, typically infrared radiations at the reference and absorption wavelengths, are directed into the front side of the material, and reflected radiations including the reference and absorption wavelengths are detected from the front side at the specular reflection angle. From the detected radiations there is produced an instrument response wherein the effects of the reference and absorption wavelengths reflected from the front side have been selectively subdued, whereby the response is indicative of the value of the property primarily as a function of the reference and absorption wavelengths reflected from the back side of the material. Typically the method is performed by additionally directing into the front side of the material a third wavelength, (e.g. 3.43 microns) to which the material exhibits a substantial opacity, additionally detecting from the front side at the specular reflection angle reflected third wavelength radiation, and producing the response so that the principal effects therein of the reference and absorption wavelengths reflected from the front side are cancelled by the effect of the third wavelength. Typically the method includes directing into the front side of the material a second reference wavelength of radiation, detecting the reflected second wavelength from the front side at the specular reflection angle, and producing from the detected first and second reference wavelengths a composite reference component of the instrument response, derived in accordance with a function which relates the relative intensities of the reflected first and second reference wavelengths to the differences in wavelength among the absorption and first and second reference wavelengths.

46 Claims, 10 Drawing Figures

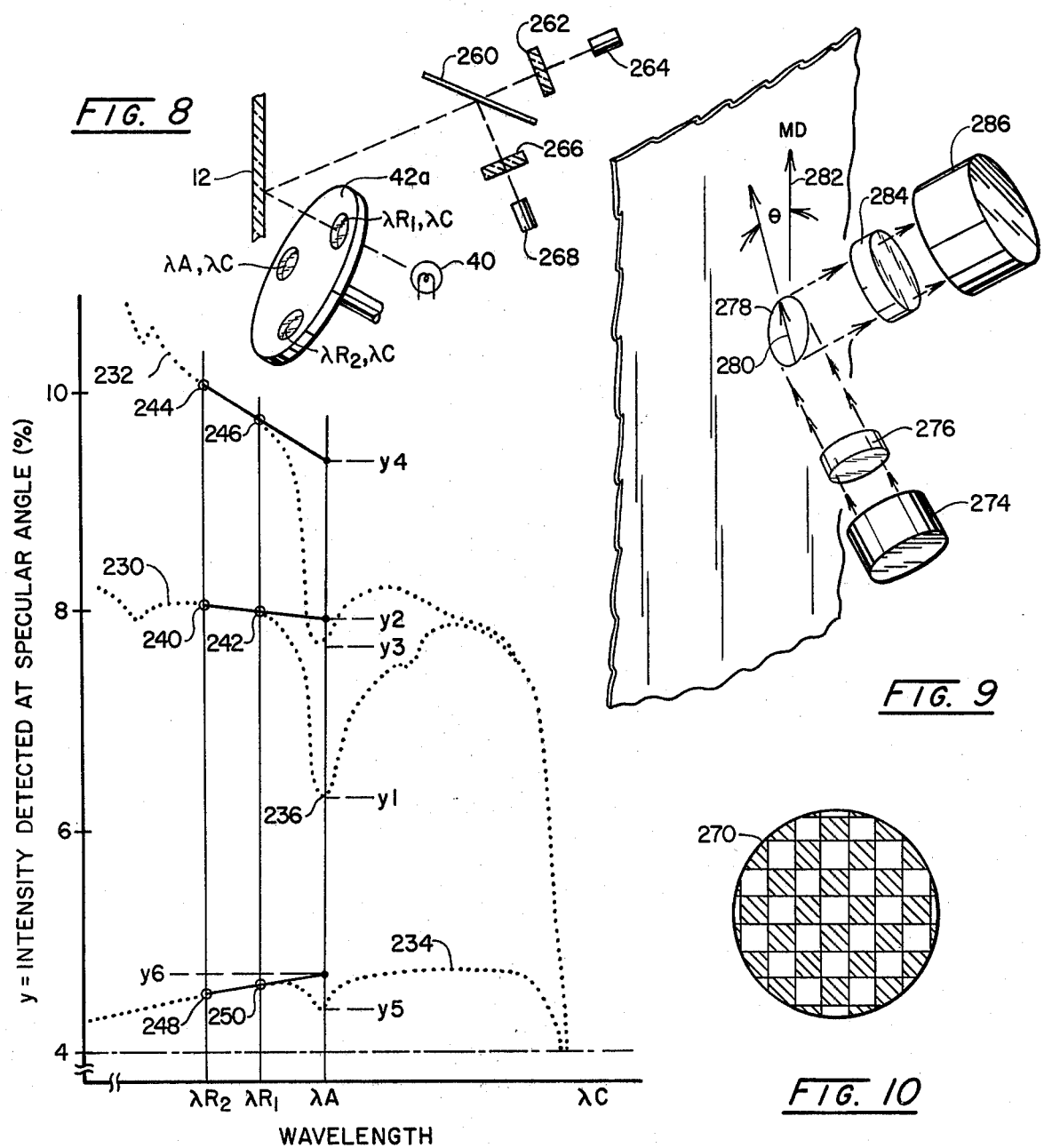
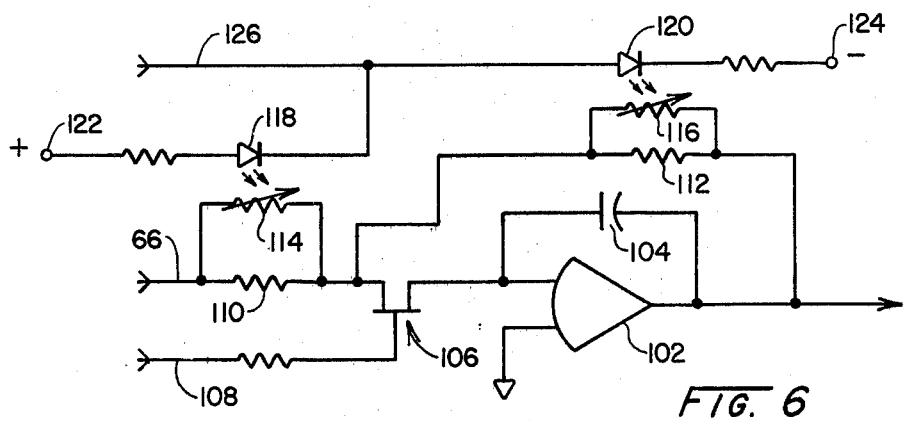

RADIATION REFLECTION METHOD AND APPARATUS PARTICULARLY FOR GAUGING MATERIALS EXHIBITING BROADBAND ABSORPTION OR SCATTERING, OR SIMILAR EFFECTS

This invention relates to methods and apparatus for gauging the properties of materials by reflected radiation. While there are many possible applications for instruments according to the invention, it will be described and illustrated in embodiments utilizing infrared radiation and adapted for measuring and controlling the thickness of blown plastic film during manufacture.

The measurement of blown film involves a rather unique set of problems. The film has two discrete sides rather than being deposited on a substrate, thus precluding the use of techniques such as those described in U.S. Pat. No. 3,693,025. For effective control in manufacture the film needs to be measured on the bubble, near its point of origin, where there is no practical access to the back side of the film for gauging purposes. A commercially successful blown film gauge utilizing two wavelengths of infrared radiation has been developed, and various features thereof are described in U.S. Pat. Nos. 3,803,414 and 3,870,884.

The operation of this commercial gauge is based on the principle that when the infrared radiation passes through the film from the front side to the back side, about four percent of the incident radiation is specularly reflected at each of the interfaces at the front and back sides. One wavelength of radiation is referred to as the reference wavelength, and is selected because it suffers no substantial absorption in a clear film. Hence about eight percent of the reference wavelength is specularly reflected from the film and is detected on the front side.

The other wavelength of radiation is referred to as the absorption wavelength, and is selected because it is absorbed by molecular resonance absorption in a "clear" film. Hence the intensity of the specularly reflected absorption wavelength radiation detected on the front side will vary between about eight percent in the case of a film approaching zero thickness to about 4 percent in the case of a film of "infinite" thickness. The four percent of each of the reference and absorption wavelengths specularly reflected from the front side contain no information concerning the thickness of the film and hence merely constitute "noise" in the measurement.

In spite of these problems, commercial infrared blown film gauges have been able to measure clear and dyed films without difficulty, but other complications arise when measuring films containing broadband radiation scattering materials such as titanium dioxide. Again satisfactory measurements have been made by combining signals from separate detectors respectively responsive to the diffusely scattered radiations and those detected at the specular reflection angle, as disclosed in U.S. Pat. No. 3,870,884.

Up to the present time, however, infrared gauging techniques have been effectively thwarted by the presence of substantial amounts of broadband radiation absorbing compounds such as the carbon black which is commonly used in the blown film stock for a line of products including the familiar greenish or brownish-black trash bags and trash can liner bags. Infrared radiation is strongly absorbed by the carbon black during the passage of the radiation from the front side of the film to the back side and from the back side to the front side.

In the case of carbon black-loaded films, commonly only a fraction of one percent of the incident radiation is returned at the specular reflection angle as a ray containing the entire range of signal information. This signal information is largely submerged in the noise constituted by the overpowering magnitude of the specular reflection from the front surface.

When the effects of the radiation specularly reflected from the front side of the film are substantially eliminated from the measurement by the methods and apparatus of the present invention, other complications are revealed. It is found that at least some of the broadband radiation absorbing particles (e.g. carbon black), and/or scattering particles (e.g. titanium dioxide) used in blown films are of such a size that their dimensions approach the infrared wavelengths. Hence there is a wavelength interaction with the particles such that the reference and absorption wavelength radiations are not affected equally by changes in the number and size of the particles in the radiation path through the film.

A somewhat similar wavelength interaction is observed in the case of some materials such as high-density polyethylene. Even though this material may not contain any broadband radiation absorbing or scattering particles, it appears that such a material has minute surface irregularities, of a size approaching the infrared wavelengths used. These irregularities cause variations in the apparent reflectivity of one or both of the surfaces on the front and back sides of the film, and the variations may not affect the reference and absorption wavelengths equally.

It is apparent from the foregoing discussion that a gauging method and apparatus capable of dealing effectively with any or all of the foregoing problems or similar problems, either individually or simultaneously, is highly desirable.

In accordance with this invention there is provided a method of, and apparatus for, gauging a property of a plastic film or other material having a front side, a back side, and characteristics including a substantial transparency to radiation at a reference wavelength and a degree of transparency depending on the value of the property at an absorption wavelength, so as to provide a useful measurement of the property in the presence or absence of detrimental effects such as those caused by a broadband absorbing or scattering substance in the material or variations in the apparent reflectivity of one or both of the surfaces on the front and back sides, comprising directing radiations at the reference and absorption wavelengths into the front side of the material, detecting from the front side at the specular reflection angle the reflected radiations including the reference and absorption wavelengths, and producing from the detected radiations an instrument response wherein the effects of the reference and absorption wavelengths reflected from the front side have been selectively subdued, whereby the response is indicative of the value of the property primarily as a function of the reference and absorption wavelengths reflected from the back side of the material.

The method typically comprises, and means are provided for, additionally directing into the front side of the material a third wavelength to which the material exhibits a substantial opacity, additionally detecting from the front side at the specular reflection angle the reflected third wavelength radiation, and producing the response so that the principal effects therein of the reference and absorption wavelengths reflected from the front side are canceled by the effect of the third wavelength.

The third wavelength radiation may be subject to a degree of absorption such that the thickness of the material is sufficient to substantially prevent third wavelength radiation which may penetrate to the back side of the material from returning to the front side. Where the molecules of the material contain carbon-hydrogen bonds, the third wavelength may comprise infrared radiation around 3.43 microns.

Typically the instrument response is a composite of a reference wavelength response, an absorption wavelength response and a third wavelength response; a first difference is effectively formed between the reference and third wavelength responses and a second difference is effectively formed between the absorption and third wavelength responses. The instrument response may be produced as a ratio effectively formed from the first and second differences.

Typically the reference wavelength provides a first reference wavelength, and methods and means are provided for also directing into the front side of the material a second reference wavelength of radiation, also detecting from the front side at the specular reflection angle the reflected second wavelength radiation, and producing from the detected first and second reference wavelengths a composite reference component of the instrument response, derived in accordance with a function which relates the relative intensities of the detected first and second reference wavelengths to the differences in wavelength among the absorption and first and second reference wavelengths. The first and second wavelengths may be detected separately. There may be produced electrically separate responses respectively indicative of the separately detected reference wavelengths, and the separate responses may be combined in accordance with the function.

The function may be a linear function that is effectively expressed by $G(R_1 - R_2) + R_1$ wherein $G$ is a constant dependent on the wavelength differences, and $R_1$ and $R_2$ are the separate responses.

The function may be determined by the characteristics of wavelength-selective filters in the path of the directed and specularly reflected radiations.

The instrument response may be computed substantially in accordance with the relationship expressed by $$I = \frac{K(R_1 - R_2) + R_1 - A}{K(R_1 - R_2) + R_1 - C}$$

where $I$ represents the instrument response, $K$ is a constant related to the differences in wavelength among the absorption and first and second wavelengths, $R_1$ and $R_2$ represent the intensities of the detected first and second reference wavelength radiations, $A$ represents the intensity of the detected absorption wavelength radiation and $C$ represents the intensity of the detected third wavelength radiation.

Typically the relationship of the instrument response to the value of the material property is substantially linearized by computing the instrument response substantially in accordance with $$I = \frac{K(R_1 - R_2) + R_1 - A}{K(R_1 - R_2) + R_1 - C - a[K(R_1 - R_2) + R_1 - A]}$$

where $a$ is a constant.

The method may comprise polarizing the radiations directed into the front side of the material, and the effects of the reference and absorption wavelengths reflected from the front side of the material may be selectively subdued by detecting a portion of the reflected radiations selectively according to their polarization. The reflected radiations may be filtered so as to substantially block the passage of radiations having the plane of polarization which is predominant in the radiations reflected from the front side of the material, and the filtered radiations may be detected.

The radiation directed into the front side of the material may be polarized at an angle $\theta$ to the direction of orientation of the molecules in the material. Where the material has been formed by a machine wherefrom the material issues in a machine direction, the angle $\theta$ may be determined by polarizing the radiation at an angle of about 45° to the machine direction in the material.

The objects of the invention are to provide an improved method and an instrument for gauging materials under conditions such that the measurement should be made by detecting radiation from one side of the material at the specular reflection angle; to provide such a method and instrument utilizing infrared radiation which is capable of measuring carbon black-loaded blown films on the bubble; to provide such a method and instrument which can measure accurately whether the material is clear, loaded with various amounts of broadband absorbers or broadband scatterers or subject to changes in apparent reflectivity on one or both sides, and to provide such a method and instrument whereby the measurements can be made using only one radiation detector.

Further objects and advantages will become apparent in the following detailed description of some typical embodiments, taken in conjunction with the appended drawings in which:

FIG. 5 is an idealized showing, on a larger scale, of a portion of the graph of FIG. 4, explaining the rationale of an extrapolated reference function derived by the use of two reference wavelengths $\lambda R_1$ and $\lambda R_2$.

FIG. 6 is a schematic circuit diagram of one of the variable-gain sample and hold circuits of FIG. 2.

FIG. 8 is a schematic diagram of apparatus for extracting first surface correction information and for performing one alternate method for incorporating an extrapolated reference function into the instrument, utilizing wavelength-selective filters.

FIG. 9 is a schematic showing of an alternate embodiment of the invention utilizing polarizing filters to subdue front surface reflection.

FIG. 10 shows the construction of one type of filter which is usable in the system of FIG. 8.

Figure 1:
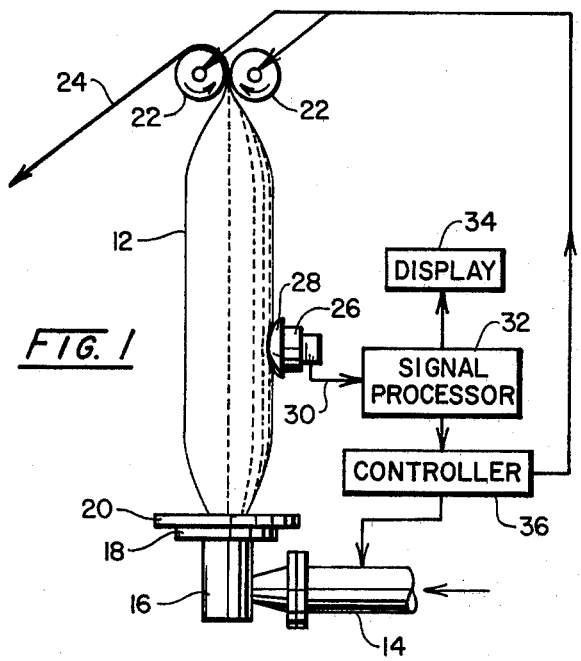
FIG. 1 illustrates a blown film extrusion machine whose product is measured and controlled by a measuring instrument according to the invention.

Referring to FIG. 1, there is shown a blown film 12 in the form of a bubble. The film bubble is continuously formed by forcing semi-fluid plastic such as low-density polyethylene from an extruder 14 through an extrusion head 16 and die 18. The bubble is shaped and initially cooled by an air ring 20 cooperating with the die 18. The hollow bubble of film 12 travels vertically from die 18 to the location of a set of pinch rolls 22 which collapse the bubble and exert tension thereon as one method of thickness control. The collapsed plastic tube 24 issuing from the pinch rolls may be fed to a windup reel and shipped for use in the manufacture of products such as dry cleaners' clothing bags, trash liner bags and the like products. Alternatively, the seamless tube of plastic may be slit and used as a single thickness of film.

For use in measuring and controlling the blown film process, an instrument according to the present invention includes a gauging head 26 with a dome-shaped shoe 28 that bears lightly against the traveling bubble of film 12. The gauging head 26 is placed along the path of travel of the film at a point as close as possible to extrusion head 18 where the thickness of the plastic has stabilized sufficiently to make the measurement representative of the final film thickness.

Signals from gauging head 26 are fed via line 30 to a signal processor 32 which develops a signal representative of the thickness of the film 12. The signal generated by signal processor 32 is fed to a suitable display apparatus 34 which may include a thickness meter or recorder. The thickness indicative signal is also fed to a controller 36. Controller 36 is operative in a known manner to supply actuating signals to one or both of extruder 14 and pinch rolls 22. Film thickness control may be achieved, for example, by controlling the operating temperature of extruder 14, by changing the speed of revolution of pinch rolls 22 in relation to the rate of plastic extrusion from extruder 14, or by changing the extruder screw speed.

Figure 2:
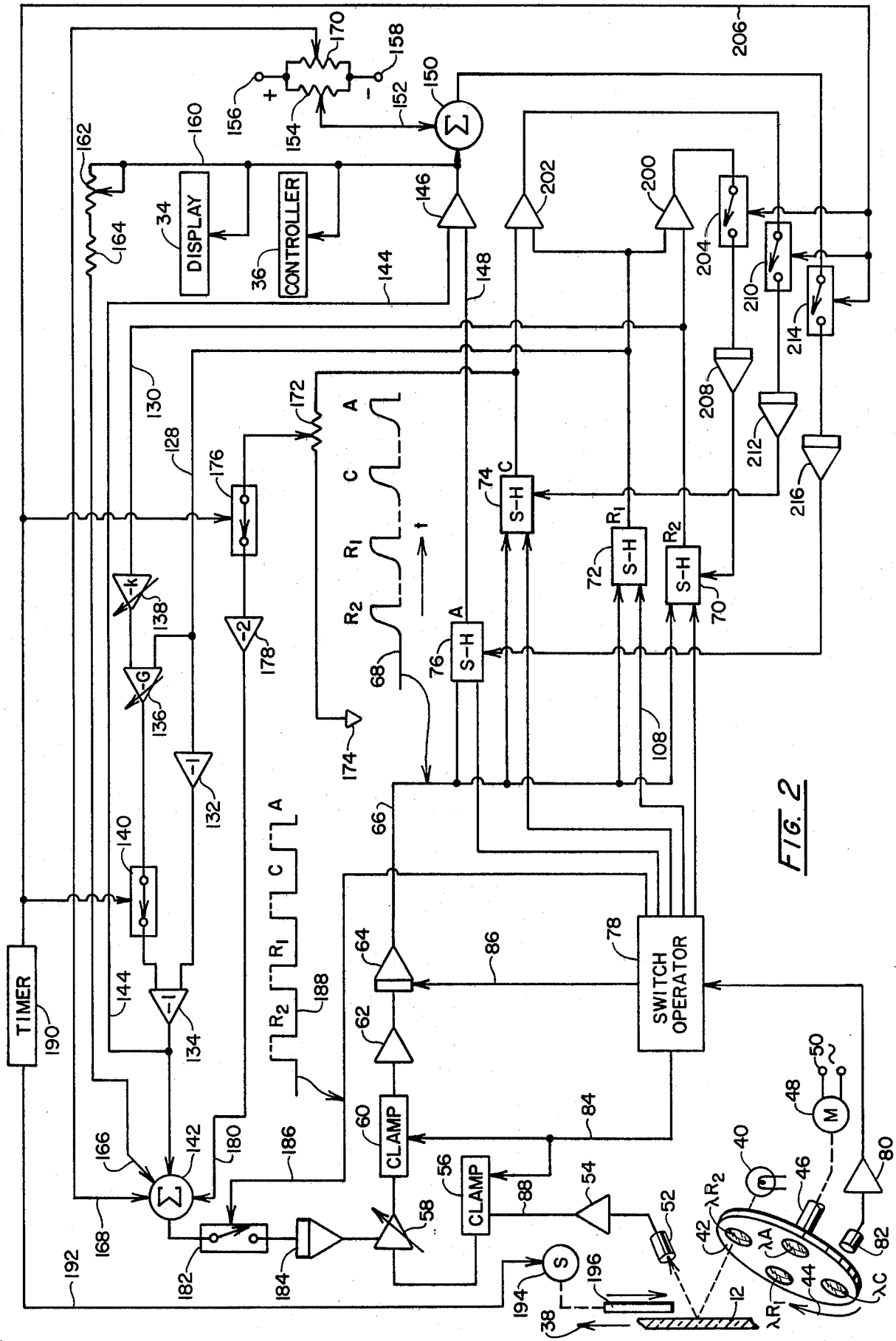
FIG. 2 is a simplified schematic diagram of the measuring instrument of FIG. 1.

Referring now to FIG. 2, the principal elements in gauging head 26 are illustrated schematically in the lower left-hand portion of the drawing. A portion of the film 12 is shown in section, traveling in the direction indicated by an arrow 38. One side of the film, herein termed the front side, is irradiated with pulses of infrared radiation from a source 40 such as an incandescent bulb. The radiation pulses are transmitted sequentially through four narrow band pass filters identified by their wavelength designations $\lambda R_2$, $\lambda R_1$, $\lambda C$ and $\lambda A$. The filters are mounted in openings equally spaced around a filter wheel 42 rotating in the direction of the arrow 44. The filter wheel is mounted on a shaft 46 driven by a synchronous motor 48 energized from an alternating voltage source connected through terminals as at 50.

By this arrangement, radiation at a reference wavelength $\lambda R_1$ and an absorption wavelength $\lambda A$ are directed into the front side of the film material 12. Interposed are pulses at a second reference wavelength $\lambda R_2$ and a further wavelength herein termed a third wavelength or correction wavelength $\lambda C$. A single radiation detector 52 is positioned to detect from the front side of the material the specularly reflected radiations including the reference and absorption wavelengths together with the second reference and correction wavelengths. It is of course possible to direct the radiations along separate paths or split beam paths and detect the different wavelength radiations with separate detectors, but typically the four wavelengths are time-multiplexed along essentially the same beam paths, whereby the use of a single detector and common signal processing circuit permits common-mode rejection and elimination of many error producing variables which would otherwise be difficult to deal with.

The sequentially detected pulses detected by detector 52 are amplified by an amplifier 54, and clamped to a base level by a switched clamp circuit 56. The signal output from clamp circuit 56 is fed through an automatic gain-controlled amplifier 58, through a second switched clamp circuit 60 and a further amplifier 62 to an integrator 64.

The output of integrator 64 on line 66 provides a series of pulses as shown by the waveform 68 plotted along a time axis $t$. As filter wheel 42 rotates, detector 52 detects a series of pulses in the order $R_2$, $R_1$, C, A . . ., and after being processed by the circuitry already described and integrated by integrator 64 integrated pulses in this sequence appear on line 66.

The integrated pulses appearing sequentially on line 66 are demultiplexed, and the final value of each pulse is held for one period of rotation of filter wheel 42 by the operation of four sample and hold (S-H) circuits 70, 72, 74 and 76 in response to switching signals from a switch operator 78. Switch operator 78 is a conventionally designed demultiplexer component similar to those used in many existing commercial instruments and prior art instruments using multiple-filter wheels as at 42 and electronic demultiplexer switching. It responds to pulses fed via an amplifier 80 from a filter wheel position sensor 82. Position sensor 82 responds to timing markers on filter wheel 42. Typically, these markers are small iron slugs located around the periphery of the wheel, and sensor 82 is a magnetic reluctance sensor.

In response to the position sensor pulses, switch operator 78 feeds switching signals to the sample and hold circuits, whereby the integrated pulse $R_2$ is sampled by sample and hold circuit 70, the $R_1$ pulse is sampled by sample and hold circuit 72, the C pulse is sampled by sample and hold circuit 74 and the A pulse is sampled by sample and hold circuit 76.

Switch operator 78 also provides clamp signals via line 84 to clamp circuits 56 and 60, as well as integrator reset pulses via line 86 to integrator 64.

Figure 7:
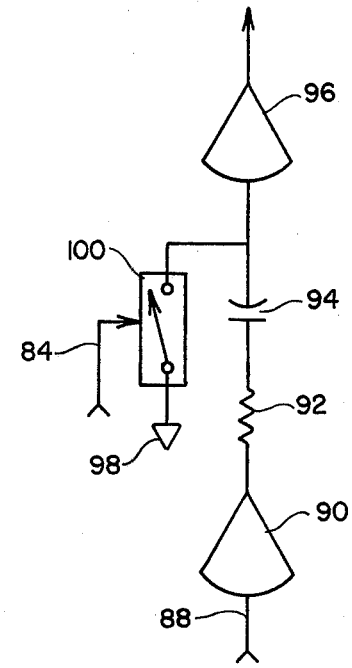
FIG. 7 is a schematic circuit diagram of one of the switched clamp circuits of FIG. 2.

FIG. 7 shows schematically one of the clamp circuits 56 and 60. The operation of clamp circuit 56 is described as follows, and it is understood that the operation of circuit 60 is identical. The signal from detector 52 and amplifier 54 is fed via line 88 into an operational amplifier 90. The output of amplifier 90 is fed via resistor 92 and capacitor 94 to a further operational amplifier 96. The input of amplifier 96 can be shorted to signal ground 98 by switch 100 in response to a signal on line 84 from switch operator 78.

Except when one of the filter apertures is in line with radiation source 40, the beam from the source 40 to the film 12 is blocked out, and the detector 52 receives no radiation from source 40. However, during the time that the path to radiation source 40 is blocked by the opaque portion of the filter wheel 42, detector 52 nevertheless receives ambient radiation, such as the ambient radiation passing through and/or emitted by the film 12. The extraneous signal generated by the detector during this time is blocked by a-c coupling. However, the a-c coupling, together with any extraneous signal generated by the circuit components results in a non-zero base level for the signal pulses applied to amplifier 96, for example. Hence, except during those times when one of the filters $\lambda R_2$, $\lambda R_1$, $\lambda C$ and $\lambda A$ is in position to direct radiation from source 40 to the surface of the film, the switch 100 is closed. This insures that the input to operational amplifier 96 is zero and that capacitor 94 is charged to the value of any non-zero signal at the output of amplifier 90 except during the time that detector 52 is actually receiving radiation from source 40 via one of the filters in the wheel 42. In a similar manner, clamp circuit 60 insures that the input to integrator 64 via amplifier 62 is clamped to the base level except during the time periods when the actual signal pulses are being received. The clamp circuits thus insure that the entire value of each signal pulse individually, and nothing but the signal pulse value, is fed to amplifiers 58 and 62.

Integrator 64 is reset by a signal fed over line 86 except when one of the signal pulses is being integrated. The integration of a signal pulse results in a waveform as shown at $R_2$ on waveform 68 after the integrated pulse has reached its peak value, and while the peak value is being maintained by the integrator, the appropriate one of the sample and hold circuits as at 70 is switched to the sample mode. As soon as the signal has been sampled by the sample and hold circuit, the integrator 64 is reset as shown by the waveforms at 68. The value of the integrated pulse is now maintained at the output of the sample and hold circuit, as shown by the legend $R_2$ at the output of sample and hold circuit 70.

A typical sample and hold circuit is shown in FIG. 6. The basic sample and hold circuit as used at 72, FIG. 2, comprises an operational amplifier 102 having a capacitor 104 connected between its input and output terminals. An input switch 106 comprising a field effect transistor (FET) is switched by an input signal on line 108 from switch operator 78 FIG. 2. When the switch 106 is turned on during the sampling operation, an input resistor 110 and a feedback resistor 112 are connected to the input of the amplifier. The circuit then behaves as an amplifier for the signal on line 66 from integrator 64, with a gain dependent on the values of the input and feedback resistors. When switch 106 is off, the amplifier 102 with feedback capacitor 104 behaves as an integrator with no input, whereby the amplifier output remains steady at the value it had when the switch 106 was turned off.

Sample and hold circuits 70, 74 and 76 are different from sample and hold circuit 72 in that they are adapted for automatic gain control. The automatic gain control elements include photoresistors 114 and 116 in parallel with input and feedback resistors 110 and 112 respectively. The resistance of the photoresistors is controlled by the amount of light generated by photodiodes 118 and 120. The photodiodes are connected between positive and negative voltage supply terminals 122 and 124 through appropriate dropping resistors. The intensity of the light emitted by photodiodes 118 and 120 is controlled by the magnitude of a signal voltage on AGC line 126. While only one photoresistor and photodiode set is sufficient to control the gain, two sets are used in the input and feedback circuits to compensate for temperature effects in the components.

It will now be assumed that there is a signal $R_2$ at the output of sample and hold circuit 70 which is indicative of the intensity of the reflected second reference wavelength radiation detected by detector 52. Similarly, a signal $R_1$ at the output of sample and hold circuit 72 is indicative of the magnitude of the reflected first reference wavelength radiation detected. Likewise at the output of sample and hold circuit 74 is a signal C indicative of the intensity of the reflected third wavelength or correction wavelength radiation detected by the detector. Finally, at the output of sample and hold circuit 76 there exists a signal A indicative of the intensity of the reflected absorption wavelength detected by the detector 52.

The $R_1$ and $R_2$ signals are fed via respective lines 128 and 130 to a circuit adapted to form what is herein termed a composite reference component of the instrument response. The $R_1$ signal on line 128 is fed through an inverter 132 to a summing amplifier 134. The same $R_1$ signal is also fed into a summing amplifier 136 having a gain of $-G$. The $R_2$ signal on line 130 is fed through an amplifier 138 having a variable gain of $-k$ to another input of amplifier 136. Amplifier 136 sums and inverts both signals, and the result is fed through a switch 140 to another input of summing amplifier 134. Amplifier 134 sums and inverts both signals to provide a signal indicative of the composite reference component. This signal is fed to a summing device 142 and is also fed over line 144 to a differential amplifier 146. Differential amplifier 146 also receives the absorption or A signal via line 148 from sample and hold circuit 76.

The output of differential amplifier 146 is fed to a summing node 150 which also receives an adjustable fixed voltage via line 152 from a potentiometer 154 connected across a constant voltage source represented by terminals 156 and 158. The output of differential amplifier 146 is also fed via line 160, a variable resistor 162 and fixed resistor 164 to another input 166 of summing node 142. Summing node 142 further receives a reference voltage $E_r$ via line 168 from a potentiometer 170 across constant voltage supply terminals 156 and 158.

The signal C indicative of the intensity of the detected third wavelength or correction wavelength, appearing at the output of sample and hold circuit 74 is fed to a potentiometer 172 connected to signal ground 174. The signal appearing at the tap of potentiometer 172 is fed through a switch 176 and an amplifier 178 to a further input 180 of summing node 142. The output of summing node 142 is fed through a switch 182 to the input of an integrator 184. The output of integrator 184 controls the gain of variable gain amplifier 58 which amplifies the radiation pulses from detector 52. The switch at the input of integrator 184 is operated by signals on line 186 from the switch operator 78. The switch is closed each time one of the outputs of sample and hold circuits 70, 72, 74 and 76 has been updated with a new value of an integrated pulse on line 66. Switch 182 is open, however, when any one of the sample and hold outputs is being updated with a new value. In other words, only the final updated integrated values of the signals are fed to integrator 184, whereas any transient signals produced by the updating process are switched out and therefore not seen by integrator 184. This permits a substantial increase in the response time of the overall system without the introduction of errors. The switching waveform on line 186 is shown at 188, indicating that switch 182 is closed between the pulses $R_2$, $R_1$, C and A shown by waveform 68.

The instrument of FIG. 2 is automatically standardized at periodic intervals, typically 15 minutes, in accordance with the teachings of U.S. Pat. No. 3,803,414. The standardization is carried out between these intervals in response to the operation of a timer 190. Timer 190 sends a signal via line 192 to energize a solenoid 194 which interposes a standardizing flag 196 between the film 12 and the filter wheel 42 and detector 52. The flag 196 simulates a material with zero thickness and returns only front-surface radiation.

The wavelength $R_1$ is the basic or first reference wavelength for the instrument. The standardization of the system adjusts the amplitude of the signals responsive to the other wavelengths so that they are all effectively equal, except for minor deviations introduced for reasons to be explained hereinafter. In the lower right-hand corner of the drawing it is seen that the $R_1$ output of sample and hold circuit 72 is fed to a pair of differential amplifiers 200 and 202 which also receive the respective $R_2$ and C outputs from sample and hold circuits 70 and 74.

The output of differential amplifier 200 is fed to a switch 204. Switch 204 is closed by a signal fed via a line 206 from the standardize timer 190 during standardization, so that the output of differential amplifier 200 is fed to an integrator 208. The output of integrator 208 constitutes the automatic gain control (AGC) input of sample and hold circuit 70. With reference to FIG. 6, for example, the output of integrator 208 would be connected to line 126.

During standardization, whenever there is a difference between the outputs of sample and hold circuits 70 and 72, the differential amplifier will provide an output to integrator 208, thus changing the integrator output in a direction such that the magnitude of the signal $R_2$ at the output of sample and hold circuit 70 will become equal to the magnitude of the signal $R_1$ at the output of sample and hold circuit 72.

In the same manner, during standardization, if there is a difference between the C output of sample and hold circuit 74 and the $R_1$ output of sample and hold circuit 72, the difference will appear at the output of differential amplifier 202, thereby feeding a signal through a switch 210 to an integrator 212 which will adjust the gain of sample and hold circuit 74 until the C output becomes equal to the $R_1$ output.

To standardize the A output of sample and hold circuit 76, it can be seen that the $R_1$ signal is fed over line 128 through amplifiers 132 and 134 and thence via line 144 to one input of differential amplifier 146. Hence, the standardization takes into account the gains of amplifiers 132 and 134. It is to be noted that during standardization the other input of amplifier 134 is disconnected by switch 140 so that the output of amplifier 136 is not involved in the standardization signal. Effectively then, during standardization, differential amplifier 146 provides an output effectively equal to the difference between the $R_1$ signal and the A signal.

This difference signal at the output of amplifier 146 is summed in summing node 150 with the constant voltage increment fed in via line 152 from potentiometer 154. For reasons to be explained subsequently, the response of the instrument is a substantially linear function of the film thickness. However, the function is not perfectly linear and hence for best calibration results the slightly non-linear response curve is approximated by the best straight line function. The bias signal fed in via line 152 is adjusted to make the straight line function pass through the point of zero thickness. Accordingly, during standardization the output of summing node 150 is equal to the difference between the $R_1$ and A signals plus the algebraically added value of the calibration bias signal. The output of the summing node is fed during standardization through a switch 214 to an integrator 216 which adjusts the gain of the sample and hold circuit 76. The gain of sample and hold circuit 76 and the magnitude of the A signal will therefore be automatically adjusted to a value such that the difference between the A signal and the $R_1$ signal is of equal magnitude and of opposite sign to the bias signal on line 152. At this time the output of summing node 150 is zero.

After the automatic standardization has been completed, standardization timer 190 discontinues the standardizing signals on lines 192 and 206. With the standardization flag 196 removed from the path of the radiation, the instrument resumes normal measurement. When the inputs to automatic gain control integrators 208, 212 and 216 are removed, the integrators will maintain their outputs as attained during standardization, thereby maintaining the gains of sample and hold circuits 70, 74 and 76 at the proper values attained during the standardization interval.

Figure 3:
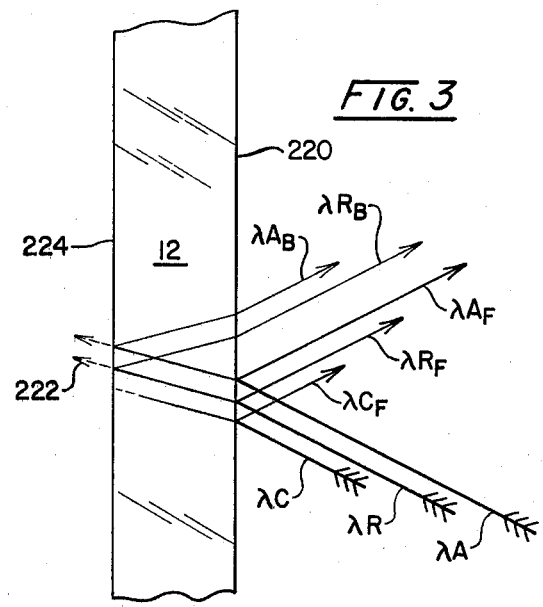
FIG. 3 is a sketch showing ray paths through a section of film 12 of FIG. 1. The usual sectioning has been omitted for clarity.

Before delving further into the operation of the circuitry of FIG. 2, it is appropriate to consider the radiation interactions with the film as they affect the operation of the instrument. Referring to FIG. 3, there are depicted three rays, $\lambda A$, $\lambda R$ and $\lambda C$ directed into the front side 220 of the film 12. This radiation is directed into the film at an angle of about 25° to the normal (not shown) and is detected by detector 52 at the specular reflection angle, which is likewise about 25°. As previously noted, in the case of $\lambda R$ about 92% of the radiation passes through the film and exits on the other side as shown by the arrow 222. About 4% of the radiation is reflected from the front surface at the specular reflection angle, forming the ray $\lambda R_F$. About another 4% is reflected from the back side 224 of the film and returned to the front side as the ray $\lambda R_B$. This ray also is reflected at the specular reflection angle, parallel to $\lambda R_F$ or coincident therewith.

The incident absorption wavelength $\lambda A$ follows a similar path through the material and suffers similar reflections. However, after two passes through the film the ray $\lambda A_B$ is substantially weaker than the reflected ray $\lambda R_B$ because the wavelength $\lambda A$ undergoes molecular resonance absorption in the film even though the film illustrated is nominally transparent. The film 12 thus exhibits a substantial transparency to reference wavelength $\lambda R$ and a degree of transparency depending on the value of the property (the thickness of the film) at the absorption wavelength $\lambda A$. The rays $\lambda A_F$ and $\lambda R_F$ contain no information concerning the thickness property since they are specularly reflected directly from the front surface 220 of the film.

The wavelength $\lambda C$ as illustrated herein is infrared radiation with a wavelength around 3.43 microns. This wavelength is one of the principal resonance wavelengths for the carbonhydrogen bonds in organic materials, and this wavelength is strongly absorbed in many organic materials. It has therefore been used to measure the temperature of plastic films as disclosed in U.S. Pat. No. 3,245,261 and to detect trace amounts of organic materials such as petroleum products as disclosed in U.S. Pat. No. 3,783,284. Because of its strong absorption by the materials formed from hydrocarbons and their derivatives, the 3.43 micron wavelength has been used to measure very thin films or organic coatings, as disclosed in U.S. Pat. Nos. 3,017,512 and 3,693,025. However, the most common plastic films having a thickness greater than about ½ mil exhibit a substantial opacity to the 3.43 micron wavelength. This is the case for such common plastics as polyethylene, poylyamide, ionomer, and ethylene vinyl acetate copoylmer (EVA). A notable exception is in the case of the polyester resin marketed under the trademark MYLAR which contains a substantially smaller number of carbon-hydrogen bonds per unit volume. While this material can be measured by the method and apparatus of the invention, it is usable only on films greater than several mils' thickness, rather than being usable down to a thickness of a half mil or less.

As shown by FIG. 3, the wavelength λC radiation has a front surface reflection component $\lambda C_F$ of an order of magnitude comparable to the other wavelengths. However, the ray which penetrates the film is rapidly absorbed, and as shown may substantially disappear before it reaches the back surface 224 of the film. In the common used blown film thicknesses of about one to three mils or less, the thickness of the material is sufficient to subtantially prevent the third wavelength or correction wavelength λC which may penetrate to the back side of the material from returning to the front side. Hence, the use of the λC wavelength provides a front surface reflection component $\lambda C_F$ which can be used to substantially cancel the effects of the noise represented by the front surface reflection $\lambda A_F$ and $\lambda R_{F_1}$ using a correction signal which is independent of the thickness of the film being measured since there is substantially no radiation at the λC wavelength returning from the back side 224 of the film.

Figure 4:
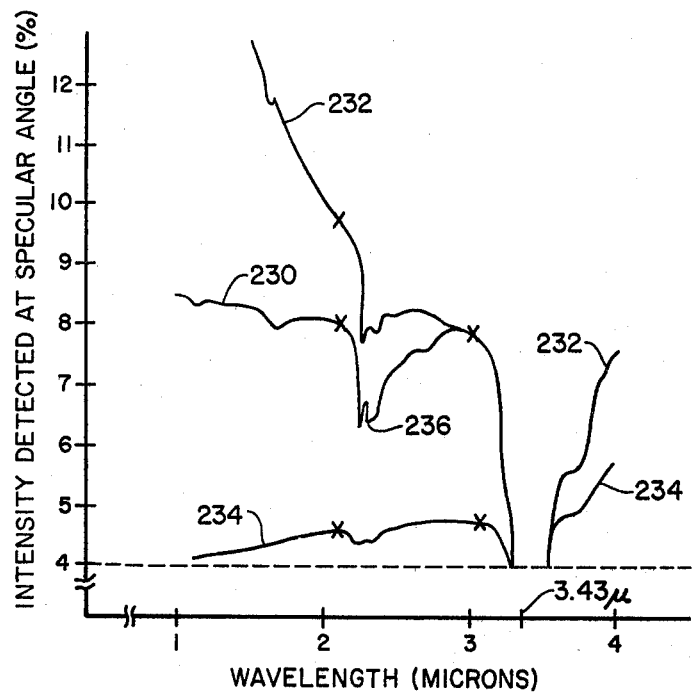
FIG. 4 is a graph showing the intensity of radiation detected at the specular reflection angle, as a percentage of the intensity of the radiation incident on the film, and as a function of wavelength, for a clear plastic film, a particular sample of titanium dioxide-loaded film and a particular sample of carbon black-loaded film.

FIG. 4 shows three curves, 230, 232 and 234 which are discontinuous around the 3.43 micron wavelengths. The shape of these curves has been estimated from data taken at 2.1 and 3.1 microns. The $x$ values on the curves represent actual sample data. The curve 230 is derived from an actual transmission spectrometer trace for clear film. The curve 232 is a curve for titanium dioxide-loaded film, and the curve 234 is a curve for carbon black-loaded film. As previously noted in the figure description, these curves depict the percentage of the incident radiation, as from the source 40 and filter wheel 42, which would be detected by detector 52 placed at the specular reflection angle, as the wavelength is varied through the portion of the spectrum shown. The dip 236 is a molecular absorption region and is prominent in the clear film curve 230. The dip is also apparent in the titanium dioxide-loaded film curve 232 and in the carbon black-loaded film curve 234.

The titanium dioxide particles which produce the shape of curve 232 constitute broadband scattering particles, and the film has high reflectivity, so that the reflection from the scattering particles adds to the front surface reflection and to the back surface reflection in the case of both the absorption and the reference wavelengths. The carbon black particles which impart the shape to curve 234 constitute a broadband absorber, so the radiation appears to sink or disappear in the material. It is to be noted that the dashed line at the 4% intensity level represents the front surface radiation, so that it is apparent that very little back surface radiation (the only radiation containing the thickness information) is returned to the front side of the material. The lack of actual data for the curves of FIG. 4 is partially accounted for by the fact that applicant's commercial spectrometer could not provide a usable signal when measuring through a substantial thickness of carbon black-loaded film. However, the data from the measuring instrument of FIG. 2 has provided sufficient data to allow plotting the estimated curves of FIG. 4, including the actual data points shown thereon.

In FIGS. 5, the curves of FIG. 4 have been idealized as to their shape. The absorption wavelength λA is located at the dip 236 of the curve 230 for the clear film. It also passes through the corresponding dip in the curves 232 and 234 for the titanium dioxide and carbon black-loaded films respectively. In the case of the common plastic films, the absorption wavelength λA is located at 2.37 to 2.38 microns. The first reference wavelength $\lambda R_1$ is located as close as possible to the absorption wavelength but in a region which is substantially free of the resonance absorption effects. This is a desirable but not absolutely essential condition. In the case of the common plastic films, the first reference wavelength $\lambda R_1$ is placed at about 2.2 microns.

The second reference wavelength of radiation $\lambda R_2$ in the illustrated example is placed in the same general region of the spectrum, but is spaced at a significant distance from the first reference wavelength $\lambda R_1$. In the case of the common plastic under discussion, satisfactory results have been obtained with the reference wavelength placed at about 1.95 microns, simply because a filter for passing the wavelength was readily available. Since 1.94 microns is an absorption wavelength for liquid water, this is to be avoided in case water is associated with the measured film. It is believed that 1.6 microns would be a satisfactory wavelength to use.

For some measurements, of some materials, it would be possible and perhaps desirable to locate the second wavelength $\lambda R_2$ on the opposite side of a dip as at 236 in the spectrum, again at a point as near as possible to the absorption band but not ordinarily in a region where the reference wavelength radiation would be substantially affected by molecular resonance absorption. In this case the specific form of the mathematical equations implemented by the circuitry of FIG. 2 would need to be changed. Such a procedure does not now appear to be a wise choice for the measurement of the common plastic films.

Two reference wavelengths are used in order to produce a composite reference component of the instrument response, which in derived in accordance with a function which relates the relative intensities of the first and second reference wavelengths to the differences in wavelength among the absorption and first and second reference wavelengths. In the case illustrated the function may be termed an extrapolated reference function, because the differential scattering or differential absorption effects on the radiations at the two reference wavelengths are projected beyond the region of the reference wavelengths to determine what the differential scattering effect would be at the absorption wavelength λA. If the reference wavelengths were to be located on opposite sides of the absorption wavelength, the function would be termed an interpolation function which would project the observed differential scattering effects at the reference wavelengths into the intermediate region to determine the absorption or scattering effect on an absorption wavelength between the two reference wavelengths.

The example herein illustrated utilizes a linear extrapolation function that is effectively expressed by $G(R_1 -$ $R_2) + R_1$ wherein $G$ is a constant dependent on the wavelength differences and $R_1$ and $R_2$ are the separate responses of detector 252 to the reference wavelengths $\lambda R_1$ and $\lambda R_2$. As shown in FIG. 5, this function projects a straight line from the point 240 (the response of the detector at $\lambda R_2$) through point 242 (the response of the detector at $\lambda R_1$) to the point $y2$. $y2$ is indicative of the value of reflected intensity which would be obtained at the wavelength $\lambda A$ if this wavelength were not affected by molecular resonance absorption, but only by the effects of other absorption or scatter in the film. This calculated intensity is to be compared with the measured intensity $y1$ which acutally includes the effect of molecular resonance absorption.

In a similar manner the function $G(R_1 - R_2) + R_1$ projects a stright line from point 244 on the curve 232 for titanium dioxide-loaded film through point 246 to determine the value $y4$ at the absorption wavelength. Likewise, the function projects a straight line from point 248 on the curve 234 for the carbon-loaded film through point 250 to determine the value $y6$ at the absorption wavelength. It is to be noted that the line through point $y6$ has a substantial positive slope; the straight line through point $y4$ has a substantial negative slope and the line through point $y2$ has a very slightly negative slope. These differences in slope are the result of the wavelength interactions with the scattering or absorbing structures in the material, which is previously noted are of such a size that at least some of the particles have dimensions of the same order of magnitude as the radiation wavelengths used.

By judicious selection of the two reference wavelengths and the magnitude of the constant G, one can approach the linear relationship shown in somewhat idealized fashion in FIG. 5 wherein the ratio $$\frac{y1}{y2} = \frac{y3}{y4} = \frac{y5}{y6}$$

holds approximately for each of the three materials. As previously indicated, the curves 230, 232 and 234 represent particular samples with specific amounts of titanium dioxide and carbon black therein. The same ratio should hold approximately for materials having any intermediate or greater or lesser amounts of the scattering and absorbing particles in the film. Since the measurement of the film thickness is based on the ratio of the extrapolated reference wavelength signal to the absorption wavelength signal, the measurement then becomes substantially independent of the presence, absence or amount of the broadband absorbing or scattering substance in the material. The function similarly takes into account, or can be made to take into account variations in the apparent reflectivity of one or both of the surfaces on the front and back sides of the material. Instead of using a linear function which can be simply processed by the analog computer system of FIG. 2, if necessary or desired for greater accuracy or convenience, the signals may be processed by digital computer techniques or more complex analog techniques using non-linear functions. For example, utilizing minicomputer or microprocessor techniques a non-linear function may be stored in a "look-up" table in the computer memory, from which the proper value can be recalled in response to a difference in the signal obtained at the two reference wavelengths.

The response of the instrument of FIG. 2 is a composite of a reference wavelength response computed by the method depicted in FIG. 5, an absorption wavelength response measured directly from the magnitude of the $\lambda A$ signal and a third wavelength response derived from the magnitude of the signal detected at the $\lambda C$ wavelength. A first difference is effectively formed between the reference and third wavelength responses in accordance with $$R' = [G(R_1 - R_2) - C \tag{1}$$

A second difference is effectively formed between the absorption and third wavelength responses in accordance with $$A' = A - C \tag{2}$$

A ratio is then effectively formed from the first and second differences in accordance with $$I = \frac{R' - A'}{R' - \alpha(R' - A')} \tag{3}$$

wherein $I$ is the instrument response.

Substituting (1) and (2) into (3) and simplifying, $$I = \frac{G(R_1 - R_2) + R_1 - A}{G(R_1 - R_2) + R_1 - C - \alpha[K(R_1 - R_2) + R_1 - A]} \tag{4}$$

It is to be noted that although this ratio is effectively formed from the first and second differences appearing in equations (1) and (2), the quantity C has dropped out of the numerator of equation (4) as a result of the algebraic manipulations.

A simplified explanation of the manner in which equation (4) is implemented in the analog computer of FIG. 2 is as follows. Assume that two signals R' and A' are passed through amplifier 58 having a gain $G_1$ so that the signals at the output of the amplifier are presented by $G_1R'$ and $G_1A'$. The difference between the two amplified signals is $G_1(R' - A')$. Assume also that the $G_1R'$ signal is compared in summing node 142 with a reference voltage $E_r$ and the difference is fed back to control the gain of amplifier 58 so that $G_1R' = E_r$. Then the gain $G_1$ of amplifier 58 is given by $$G_1 = E_r/R'$$

The difference signal $G_1(R' - A')$ is then given by $$G_1(R' - A') = E_r \frac{(R' - A')}{R'}.$$

If this quantity is used to produce the instrument response I and $E_r$ is taken to be unity and if the R' and A' values from equations (1) and (2) are substituted, then $$I = \frac{K(R_1 - R_2) + R_1 - A}{K(R_1 - R_2) + R_1 - C}$$

If a small fraction $\alpha$ (determined by the setting of variable resistor 162) is then fed back to further modify the gain of amplifier 58, one obtains a substantially linearized response in accordance with $$I = \frac{K(R_1 - R_2) + R_1 - A}{K(R_1 - R_2) + R_1 - C - \alpha[K(R_1 - R_2) + R_1 - A]}$$

The composite reference component of the instrument response is formed as previously described by amplifiers 132, 134, 136 and 138. The gain $-k$ of amplifier 138 does not appear in the foregoing simplified calculations because it is only a trimming adjustment used to take into account the fact that the relative intensities of $\lambda R_1$ and $\lambda R_2$ received when the standardizing flag 196 is viewed by the detector 52, are not the same as they are when the detector 52 is viewing the actual film material. The gain $-k$ of amplifier 138 can be set by placing a sample of clear film in front of the detector 52 when the instrument is in the normal measuring mode. Noting the reading on display system 34, the gain of amplifier 136 is varied through a substantial portion of its range. The gain $-k$ amplifier 138 is adjusted to a point where the reading on display 34 does not change when the gain of amplifier 136 is varied.

To set the third wavelength correction adjustment on potentiometer 172, a sample of the clear plastic film is placed in measuring position in the guage. While observing the display 34, a sheet of ordinary glass or tetrafluoroethylene resin plastic (TEFLON) is placed against the back side 224 of the film. The glass, for example, does not preferentially absorb or scatter the absorption $\lambda A$ and reference $\lambda R$ wavelengths, but simply increases the magnitude of the back surface radiations $\lambda A_B$ and $\lambda A_B$ returned to the detector side. The front surface radiation at $\lambda C_F$ is not affected by the presence of the glass, since $\lambda C$ is substantially completely absorbed by the measured clear plastic film 12. The setting of potentiometer 172 is adjusted until there is no change in reading on the display 34 when the glass is removed or replaced from its position on the back side of the clear film sample 12. This is an indication that the effects of the reference and absorption wavelengths reflected from the front side of the film are being canceled by the effect of the third wavelength.

The gain $-G$ of amplifier 136 is adjusted after the display 34 has been calibrated for clear film samples, using the conventional gain and suppression adjustments provided in the display system per se. When materials with the broadband scattering substance, (e.g., $TiO_2$) broadband absorbing substance (e.g., carbon black) or surface effects (e.g., high density polyethylene) are measured, the calibrated display should provide accurate readings. If this is not the case, the gain $-G$ of amplifier 136 is adjusted to correct the readings for these materials. The best compromise setting may be used where the nature of the materials and the filters used in filter wheel 42 do not allow the instrument to perform perfectly as shown by FIG. 5. Normally if any grade switching is necessary on account of differences in the film materials measured, this is done in display system 34 and the gain of amplifier 136 need not be disturbed. Where the same instrument is used to measure all materials including some containing broadband scatterers, or broadband absorbers as well as some containing certain surface effects, it may be necessary to provide a gain switch arrangement for amplifier 136 for use when changing to or from a material having the surface effects.

FIG. 8 shows one way in which the signals can be combined optically to substantially cancel the first surface radiation. In this case the filter wheel 42a contains three filters which are composite filters that can be constructed, for example, as shown in FIG. 10. It can be assumed that the shaded blocks in FIG. 10 represent filter portions passing only $\lambda C$, whereas the clear squares represent filter portions that may pass either $\lambda A$, or $\lambda R_1$ or $\lambda R_2$.

In FIG. 8 one filter passes $\lambda A$ and $\lambda C$, another filter passes $\lambda R_1$ and $\lambda C$ and the third filter passes $\lambda R_2$ and $\lambda C$.

The radiation reflected at the specular angle from film 12 is transmitted to a beam splitter 260 which directs part of the beam through a filter 262 to a detector 264. It may be assumed that filter 262 blocks all radiation except $\lambda C$ and that therefore only $\lambda C$ radiation is detected by detector 264.

There are two alternative constructions for filter 266. In one case, filter 266 passes to the detector the reference wavelengths $\lambda R$, the absorption wavelength $\lambda A$ and the correction wavelength $\lambda C$. Since $\lambda C_F = \lambda A_F$, twice the value of $\lambda C$ detected by detector 264 is subtracted, by means not shown, from the output of detector 268 in order to provide a remaining signal equal to $\lambda A_b$ which contains the thickness information.

In a second arrangement, filter 266 may be arranged to pass only the reference wavelengths $\lambda R$ and the absorption wavelength $\lambda A$. In this case, the signal detected by detector 264 is simply subtracted from the output of detector 268 to leave as a remainder the thickness-indicative signal $\lambda A_B$. The filters as in FIG. 10 may be trimmed optically in order to balance the signal levels. For example, a filter can be arranged to pass more of the $\lambda C$ radiation than the other radiation and then the filter can be sprayed with an organic material containing carbon-hydrogen bonds so as to preferentially absorb the excess $\lambda C$ radiation until the proper balance is achieved. The electrical signal levels generated by detectors 264 and 268 can be amplified or attenuated as desired according to prior art techniques before they are combined to produce the final measurement.

FIG. 9 illustrates a still further apparatus arrangement whereby the method of the invention may be carried out. Radiation from a source 274 is passed through a polarizing filter 276 to project a spot 278 of polarized radiation onto the front surface of the film. By the use of a polarizing filter 284, the detector 286 at the specular reflection angle is caused to detect a portion of the reflected radiations selectively according to their polarization.

The filter 284 is arranged to substantially block the passage of radiation having that plane of polarization which is predominant in the radiation reflected from the front side of the material. Ideally, the radiation passing through filter 276 to the material would be 100% polarized and the radiations reflected from the front surface of the film would remain polarized. The plane of polarization of filter 284 could then block all front surface radiation from the detector 286. The radiation penetrating the film and being reflected from the back side thereof would be depolarized by the film material and a substantial amount of the depolarized radiation would be detected by detector 286 to effect the measurement of the material.

In the practical case, utilizing the best commercial polarizing filters as at 276, the radiation is only about 90% polarized, and after taking into account the fact that all of the radiation from the front surface of the material does not remain polarized, it is found that a relatively large amount of front surface radiation is still present to affect the measurement. In the case of carbon black-loaded films, the front surface radiation is still very large by comparison with the useful signal radiation reflected from the back side. While a noticeable improvement in the performance of existing guages has been made by an instrument in accordance with FIG. 9 using presently available commercial filters, the method has not as yet proved economically and technically feasible for ordinary commercial use because of the imperfect degree of polarization provided by the present commercial polarizing filters. At sometime in the future, with the development of better polarizers, the arrangement of FIG. 9 could become commercially important.

As shown by FIG. 9, the radiation directed into the front side of the material should be polarized at an angle θ, as in the direction of arrow 278, to the direction of orientation of the molecules in the material. In the case of most blown films, as shown the radiation is polarized at an angle θ of about 45° to the machine direction MD of the material.

While the invention has been described and illustrated by particular procedures and particular apparatus, the showing and description is meant to be illustrative only and not restrictive, since many modifications can be made without departing from the spirit and scope of the invention.

What is claimed is:

1. The method of gauging a property of a plastic film or other material having a front side, a back side, and characteristics including a substantial transparency to radiation at a reference wavelength and a degree of transparency depending on the value of the property at an absorption wavelength, so as to provide a useful measurement of the property in the presence or absence of detrimental effects such as those caused by a broadband absorbing or scattering substance in the material or variations in the apparent reflectivity of one or both of the surfaces on the front and back sides, comprising
   directing radiations at the reference and absorption wavelengths into the front side of the material,
   detecting from the front side at the specular reflection angle the reflected radiation including the reference and absorption wavelengths, and
   producing from the detected radiations an instrument response wherein the effects of the reference and absorption wavelengths reflected from the front side have been selectively subdued, whereby the response is indicative of the value of the property primarily as a function of the reference and absorption wavelengths reflected from the back side of the material.

2. A method as in claim 1 comprising
   additionally directing into the front side of the material a third wavelength to which the material exhibits a substantial opacity.
   additionally detecting from the front side at the specular reflection angle the reflected third wavelength radiation, and
   producing the response so that the principal effects therein of the reference and absorption wavelengths reflected from the front side are canceled by the effect of the third wavelength.

3. A method as in claim 2 wherein the third wavelength radiation is subject to a degree of absorption such that the thickness of the material is sufficient to substantially prevent third wavelength radiation which may penetrate to the back side of the material from returning to the front side.

4. A method as in claim 3 wherein the molecules of the material contain carbon-hydrogen bonds, and wherein the third wavelength comprises infrared radiation around 3.43 microns.

5. A method as in claim 2 wherein the instrument response in a composite of a reference wavelength response, an absorption wavelength response and a third wavelength response, comprising effectively forming a first difference between the reference and third wavelength responses and a second difference between the absorption and third wavelength responses.

6. A method as in claim 5 comprising producing the instrument response as a ratio effectively formed from the first and second differences.

7. A method as in claim 1 wherein the reference wavelength provides a first reference wavelength, comprising
   also directing into the front side of the material a second reference wavelength of radiation,
   also detecting from the front side at the specular reflection angle the reflected second wavelength radiation, and
   producing from the detected first and second reference wavelengths a composite reference component of the instrument response, derived in accordance with a function which relates the relative intensities of the detected first and second reference wavelengths to the differences in wavelength among the absorption and first and second reference wavelengths.

8. A method as in claim 7 wherein the first and second wavelengths are detected separately.

9. A method as in claim 8 comprising electrically producing separate responses respectively indicative of the separately detected reference wavelengths, and combining the separate responses in accordance with the function.

10. A method as in claim 9 wherein the function is a linear function that is effectively expressed by $G(R_1 - R_2) + R_1$ wherein G is a constant dependent on the wavelength differences, and $R_1$ and $R_2$ are the separate responses.

11. A method as in claim 7 wherein the function is determined by the characteristics of wavelength-selective filters in the path of the directed and specularly reflected radiations.

12. A method as in claim 7 comprising
   additionally directing into the front side of the material a third wavelength to which the material exhibits a substantial opacity.
   additionally detecting from the front side at the specular reflection angle the reflected third wavelength radiation, and
   producing the instrument response so that the principal effects therein of the composite reference and absorption wavelengths reflected from the front side are canceled by the effect of the third wavelength.

13. A method as in claim 12 wherein the third wavelength radiation is subject to a degree of absorption such that the thickness of the material is sufficient to substantially prevent third wavelength radiation which may penetrate to the back side of the material from returning to the front side.

14. A method as in claim 13 wherein the molecules of the material contain carbon-hydrogen bonds, and wherein the third wavelength comprises infrared radiation around 3.43 microns.

15. A method as in claim 7 wherein the instrument response is formed from a composite reference wavelength response, an absorption wavelength response and a third wavelength response, comprising effectively forming a first difference between the composite reference and third wavelength responses and a second difference between the absorption and third wavelength responses.

16. A method as in claim 15 comprising producing the instrument response as a ratio effectively formed from the first and second differences.

17. A method as in claim 16 wherein the instrument response is computed substantially in accordance with the relationship expressed by $$I = \frac{K(R_1 - R_2) + R_1 - A}{K(R_1 - R_2) + R_1 - C}$$

wherein $I$ represents the instrument response, $K$ is a constant related to the differences in wavelength among the absorption and first and second wavelengths, $R_1$ and $R_2$ represent the intensities of the detected first and second reference wavelength radiations, A represents the intensity of the detected absorption wavelength radiation and C represents the intensity of the detected third wavelength radiation.

18. A method as in claim 17 wherein the relationship of the instrument response to the value of the material property is substantially linearized by computing the instrument response substantially in accordance with $$I = \frac{K(R_1 - R_2) + R_1 - A}{K(R_1 - R_2) + R_1 - C - a[K(R_1 - R_2) + R_1 - A]}$$

wherein $a$ is a constant.

19. A method as in claim 15 wherein the molecules of the material contain carbon-hydrogen bonds, and wherein the third wavelength comprises infrared radiation around 3.43 microns.

20. A method as in claim 1 comprising polarizing the radiations directed into the front side of the material, and wherein the effects of the reference and absorption wavelengths reflected from the front side of the material are selectively subdued by detecting a portion of the reflected radiations selectively according to their polarization.

21. A method as in claim 20 comprising filtering the reflected radiations so as to substantially block the passage of radiations having that plane of polarization which is predominant in the radiations reflected from the front side of the material, and detecting the filtered radiations.

22. A method as in claim 20 wherein the radiation directed into the front side of the material is polarized at an angle $\theta$ to the direction of orientation of the molecules in the material.

23. A method as in claim 22 for gauging a material formed by a machine wherefrom the material issues in a machine direction, wherein the angle $\theta$ is determined by polarizing the radiation at an angle of about 45° to the machine direction of the material.

24. Apparatus for gauging a property of a plastic film or other material having a front side, a back side, and characteristics including a substantial transparency to radiation at a reference wavelength and a degree of transparency depending on the value of the property at an absorption wavelength, so as to provide a useful measurement of the property in the presence or absence of detrimental effects such as those caused by a broadband absorbing or scattering substance in the material or variations in the apparent reflectivity of one or both of the surfaces on the front and back sides, comprising
means for directing radiations at the reference and absorption wavelengths into the front side of the material,
means for detecting from the front side at the specular reflection angle the reflected radiations including the reference and absorption wavelengths, and
means for producing from the detected radiations an instrument response wherein the effects of the reference and absorption wavelengths reflected from the front side have been selectively subdued, whereby the response is indicative of the value of the property primarily as a function of the reference and absorption wavelengths reflected from the back side of the material.

25. Apparatus as in claim 24 comprising
means for additionally directing into the front side of the material a third wavelength to which the material exhibits a substantial opacity,
means for additionally detecting from the front side at the specular reflection angle the reflected third wavelength radiation, and
means for producing the response so that the principal effects therein of the reference and absorption wavelengths reflected from the front side are canceled by the effect of the third wavelength.

26. Apparatus as in claim 25 wherein the third wavelength radiation is subject to a degree of absorption such that the thickness of the material is sufficient to substantially prevent third wavelength radiation which may penetrate to the back side of the material from returning to the front side.

27. Apparatus as in claim 26 for gauging a material whose molecules contain carbon-hydrogen bonds, and wherein the third wavelength comprises infrared radiation around 3.43 microns.

28. Apparatus as in claim 25 wherein the instrument response is a composite of a reference wavelength response, an absorption wavelength response and a third wavelength response, comprising means for effectively forming a first difference between the reference and third wavelength responses and a second difference between the absorption and third wavelength responses.

29. Apparatus as in claim 28 comprising means for producing the instrument response as a ratio effectively formed from the first and second differences.

30. Apparatus as in claim 24 wherein the reference wavelength provides a first reference wavelength, comprising
means for also directing into the front side of the material a second wavelength of radiation,
means for also detecting from the front side at the specular reflection angle the reflected second wavelength radiation, and
means for producing from the detected first and second reference wavelengths a composite reference component of the instrument response, dervied in accordance with a function which relates the relative intensities of the detected first and second reference wavelengths to the differences in wavelength among the absorption and first and second reference wavelengths.

31. Apparatus as in claim 30 comprising means for detecting the first and second wavelengths separately.

32. Apparatus as in claim 31 comprising means for electrically producing separate responses respectively indicative of the separately detected reference wavelengths, and means for combining the separate responses in accordance with the function.

33. Apparatus as in claim 32 wherein the function is a linear function that is effectively expressed by $G(R_1 - R_2) + R_1$ wherein G is a constant dependent on the wavelength differences, and $R_1$ and $R_2$ are the separate responses.

34. Apparatus as in claim 30 comprising wavelength-selective filters in the path of the directed and specularly reflected radiations for determining the function.

35. Apparatus as in claim 30 comprising
    means for additionally directing into the front side of the material a third wavelength to which the material exhibits a substantial opacity,
    means for additionally detecting from the front side at the specular reflection angle the reflected third wavelength radiation, and
    means for producing the instrument response so that the principal effects therein of the composite reference and absorption wavelengths reflected from the front side are canceled by the effect of the third wavelength.

36. Apparatus as in claim 35 wherein the third wavelength radiation is subject to a degree of absorption such that the thickness of the material is sufficient to substantially prevent third wavelength radiation which may penetrate to the back side of the material from returning to the front side.

37. Apparatus as in claim 35 for gauging a material whose molecules contain carbon-hydrogen bonds, and wherein the third wavelength comprises infrared radiation around 3.43 microns.

38. Apparatus as in claim 30 comprising means for forming the instrument response from a composite reference wavelength response, an absorption wavelength response and a third wavelength response, including means for forming a first difference between the composite reference and third wavelength responses and a second difference between the absorption and third wavelength responses.

39. Apparatus as in claim 38 comprising means for producing the instrument response as a ratio effectively formed from the first and second differences.

40. Apparatus as in claim 39 comprising means for computing the instrument response substantially in accordance with the relationship expressed by $$I = \frac{K(R_1 - R_2) + R_1 - A}{K(R_1 - R_2) + R_1 - C}$$

wherein $I$ represents the instrument response, $K$ is a constant related to the differences in wavelength among the absorption and first and second wavelengths, $R_1$ and $R_2$ represent the intensities of the detected first and second reference wavelength radiations, $A$ represents the intensity of the detected absorption wavelength radiation and C represents the intensity of the detected third wavelength radiation.

41. Apparatus as in claim 40 wherein the relationship of the instrument response to the value of the material property is substantially linearized, comprising means for computing the instrument response substantially in accordance with $$I = \frac{K(R_1 - R_2) + R_1 - A}{K(R_1 - R_2) + R_1 - C - a[K(R_1 - R_2) + R_1 - A]}$$

wherein $a$ is a constant.

42. Apparatus as in claim 38 for gauging a material whose molecules contain carbon-hydrogen bonds, and wherein the third wavelength comprises infrared radiation around 3.43 microns.

43. Apparatus as in claim 24 comprising means for polarizing the radiations directed into the front side of the material, and means for detecting a portion of the reflected radiations selectively according to their polarization so as to selectively subdue the effects of the reference and absorption wavelengths reflected from the front side of the material.

44. Apparatus as in claim 43 comprising means for filtering the reflected radiations so as to substantially block the passage of radiations having the plane of polarization which is predominant in the radiations reflected from the front side of the material, and means for detecting the filtered radiations.

45. Apparatus as in claim 43 wherein the radiation directed into the front side of the material is polarized at an angle 0 to the direction of orientation of the molecules in the material.

46. Apparatus as in claim 45 for gauging a material formed by a machine wherefrom the material issues in a machine direction, wherein the radiation is polarized at an angle of about 45° to the machine direction of the material to determine the angle 0.

* * * * *